United States Patent [19]

Fong et al.

[11] Patent Number: 4,592,809

[45] Date of Patent: Jun. 3, 1986

[54] ELECTROPLATING COMPOSITION AND PROCESS AND SURFACTANT COMPOUND FOR USE THEREIN

[75] Inventors: Jaan J. Fong, Woodbury, Minn.; Donald H. Becking, Southington, Conn.

[73] Assignee: MacDermid, Incorporated, Waterbury, Conn.

[21] Appl. No.: 762,940

[22] Filed: Aug. 6, 1985

[51] Int. Cl.$^4$ .................... C07C 143/38; C25D 3/22; C25D 3/56

[52] U.S. Cl. .................. 204/44.2; 204/45.1; 204/55 R; 204/DIG. 2; 260/512 C

[58] Field of Search .................. 260/512 C, 512 R; 204/DIG. 2, 45.1, 44.2, 55 R, 55 Y

[56] References Cited

U.S. PATENT DOCUMENTS

| | | | |
|---|---|---|---|
| 1,421,722 | 7/1922 | Römer et al. | 260/512 R X |
| 3,729,394 | 4/1973 | Hsu et al. | 204/55 R |
| 3,766,024 | 10/1973 | Yamagishi et al. | 204/55 R |
| 3,787,296 | 1/1974 | Hayashida et al. | 204/55 R |
| 4,070,256 | 1/1978 | Hsu et al. | 204/55 R |
| 4,502,926 | 3/1985 | Barber | 204/45.1 |
| 4,512,856 | 4/1985 | Paneccasio | 204/55 R |
| 4,514,267 | 4/1985 | Lash | 204/44.2 |
| 4,515,663 | 5/1985 | Strom et al. | 204/44.2 |
| 4,528,075 | 7/1985 | Anchor et al. | 204/55 R |
| 4,532,051 | 7/1985 | Nuckels et al. | 252/8.55 D |
| 4,541,906 | 9/1985 | Martin | 204/55 R |

FOREIGN PATENT DOCUMENTS

| | | | |
|---|---|---|---|
| 1146588 | 3/1969 | United Kingdom | 260/512 R |
| 1209286 | 10/1970 | United Kingdom | 260/512 C |

*Primary Examiner*—Gerald L. Kaplan
*Attorney, Agent, or Firm*—St. Onge, Steward, Johnston & Reens

[57] ABSTRACT

Non-ionic surfactants prepared by reaction of ethoxylated bisphenols and sulfating agents such as sulfamic acid, sulfuric acid and chlorosulfonic acid are employed in metal electroplating baths and processes to increase the useful operating temperature limits of the baths in comparison to those using other non-ionic surfactants. The surfactants are particularly useful as additives in acid zinc electroplating baths, and especially acid zinc electroplating baths either completely devoid of ammonium ion or containing low amounts of ammonium ion.

35 Claims, No Drawings

ELECTROPLATING COMPOSITION AND PROCESS AND SURFACTANT COMPOUND FOR USE THEREIN

BACKGROUND OF THE INVENTION

This invention relates to the field of metal electroplating and, more particularly, to the utilization of particular surfactants and surfactant compositions in the preparation of electroplating baths and use of such baths for electroplating metals onto suitable surfaces.

The art of the electroplating or electrodepositing of a metal or metal alloy from solution onto surfaces of a suitable substrate or workpiece is, of course, well known and well developed for a wide range of metals, alloys and substrates. The fundamental process involves immersion of the workpiece in a suitably prepared electroplating bath and application of a voltage across the cathodic workpiece and an anode which also is immersed in the bath. The essential bath components comprise an aqueous admixture of a source of the metal ion to be deposited and an electrolyte. Many other optional bath components are, of course, known and used to attain particular effects in electroplating such as increased efficiency of plating, stabilization of bath components, pH adjustment, improved brightness or ductility or adherence of the metal deposit, and the like.

Ideally, all components of an electroplating bath will be water soluble at the concentrations and conditions employed so that an equal distribution of components can be attained. As is known, however, this ideal is not usually realized and many of the special components employed to attain particular effects are either insoluble in water or only difficultly soluble. For this reason, it is common to include as an essential component in the electroplating bath a surfactant (surface active agent) to aid in solubilizing bath components and/or to promote stable, even distribution of bath components.

The operating conditions for electroplating from aqueous solution can vary widely depending upon the metal to be plated, substrate, bath composition, and the like. In general, the operating temperature of the bath is desirably high so as to increase plating efficiency. However, the ability to employ high temperatures in electroplating is severely mitigated by limitations imposed by the compositional make-up of the electroplating bath. In particular, surfactant-containing aqueous electroplating baths have associated with them a particular "cloud point", i.e., a temperature at and above which the surfactant component oils or salts out from solution (exhibited by turbidity or cloudiness in the bath). Attempted operation at or above the cloud point of the bath will lead to extremely poor electroplated deposits because of the non-uniformity of bath component composition.

In formulating aqueous electroplating baths, additives and techniques employed to attain a particular advantage can have adverse effects on other bath or operating properties. A good example of this is seen in acid zinc electroplating baths. Early formulations of such baths utilized an ammonium salt as the soluble electrolyte and a non-ionic surfactant, and as so formulated, were capable of operation at relatively high and efficient temperature. Later formulations of these baths were designed to eliminate or substantially reduce ammonium ion (and the disposal problems associated with its ability to complex heavy metals) by using a non-ammoniated electrolyte and other compounds (e.g., boric acid) to compensate for lost ammonium ion buffering capacity. These reformulations, however, resulted in substantial lowering of the cloud point of the bath such that attempted operation at temperatures used in ammoniated formulations caused precipitation of the non-ionic surfactant and consequently ineffective plating. The need to operate these baths at reduced temperatures to avoid these problems is a limitation on plating efficiency and on operating flexibility.

For any fundamental bath formulation, it is highly desirable to have flexibility in operating temperature conditions. In this way, other operating conditions such as current density and current efficiency and various formulation characteristics can be optimized without concern for inherently limiting restrictions imposed by operating temperatures and cloud points. Moreover, bath operating temperature flexibility provides insurance against unexpected temperature rises (e.g., climate changes or equipment malfunction) which, if exceeding the cloud point, would otherwise lead to poor plating and/or require a complete shut-down of the operation. In accomplishing this flexibility through choice of particular surfactants which exhibit a desirably high cloud point in the desired media, it is of course necessary that the surfactant be capable of serving its intended purpose and not otherwise adversely affect bath, plating or deposition characteristics.

SUMMARY OF THE INVENTION

The specific aim of the invention is to provide an acid zinc electroplating bath containing a non-ionic surfactant which is capable of operation over a wide range of temperatures, including relatively elevated temperature, while providing deposits which are acceptable in all respects. Even more specifically, this aim was sought to be attained in an acid zinc electroplating bath in which a non-ammoniated electrolyte is employed (which bath can be completely devoid of ammonium ion or possess only a low amount of ammonium ion relative to the amount of ammonium which would be present if an ammonium salt were relied upon as the electrolyte).

In achieving these goals, a unique surfactant compound was discovered which has applicability not only to acid zinc baths of the type described, but also to any metal electroplating bath in which a non-ionic surfactant component is employed, as, for example, in acid copper plating baths. Baths containing the surfactant of the invention also exhibit high tolerance to iron contamination, reduced foaming and improved throwing power at low chloride levels.

According to the invention, electroplating baths are provided which contain a soluble source of the metal to be deposited, a soluble electrolyte and a surfactant of the formula:

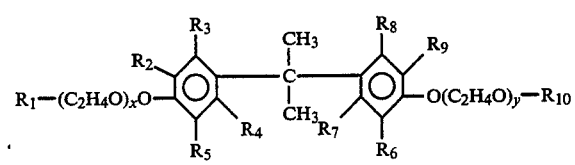

wherein:
x and y are integers from 1 to 39, and the sum of x+y is from 2 to 78;
$R_1$ through $R_{10}$ are H or $SO_3X$, with the proviso that at least one of $R_1$ through $R_{10}$ must be $SO_3X$; and X is any monovalent cation, such as NH₄, H, Na, K or Li.

As described in further detail hereinafter, the surfactant according to the invention can be prepared by reaction of an ethoxylated bisphenol and a sulfating agent such as sulfamic acid, sulfuric acid or chlorosulfonic acid.

In the preferred embodiments of the invention, the electroplating bath is an acid zinc electroplating bath which is completely devoid of ammonium ion or contains only low amounts of ammonium ion. In such baths, use of the surfactant of the invention permits operation at temperatures of up to about 160° F., in contrast to the need for operation at temperature below about 100° F. for comparable baths using known surfactants.

PRIOR ART

U.S. Pat. No. 3,729,394 discloses an ammonium ion-based, acid-zinc electroplating bath employing as a surfactant a non-ionic block copolymer of ethylene oxide and propylene oxide. Certain anionic N-(alkyl sulfonyl) glycine compounds can be employed in conjunction with the block copolymer, as may anionic condensates of naphthalene/sulfonic acid.

U.S. Pat. No. 3,766,024 discloses an ammonium ion-based, acid-zinc electroplating bath which may contain, inter alia, ethoxylated α-naphthol sulfonic acid in aid of the provision of a glossy surface appearance.

U.S. Pat. No. 3,787,296 discloses a non-poisonous (i.e., cyanide-free) zinc electroplating bath based on ammonium salts and containing a sulfate compound of a polyether as part of a series of additives to improve current efficiency.

U.S. Pat. No. 4,070,256 discloses acid-zinc electroplating baths based upon non-ammoniated electrolytes and employing non-ionic polyoxyalkylated surfactants.

U.S. Pat. No. 4,512,856 discloses an acid-zinc electroplating bath of increased cloud point containing a non-surfactant substituted polyhydric alcohol having ethoxylated and/or propoxylated hydroxyl groups as a grain-refining agent.

U.S. Pat. No. 4,515,663 discloses an acid-zinc electroplating bath containing a polyhydroxy additive agent which can exhibit —SO₃H moieties as a means for reducing the formation of polyborate compounds.

U.S. Pat. No. 4,514,267 relates to a make-up solution for zinc electroplating baths in which an alkyl phenyl sulfonate is used as a solubilizing agent for a hydrophobic organic brightener.

DETAILED DESCRIPTION OF THE INVENTION

In preparing the surfactant of the invention an ethoxylated bisphenol, prepared by reaction of bisphenol A with ethylene oxide, is provided which corresponds to the formula:

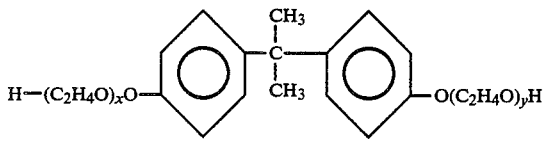

In the formula, x and y are integers from 1 to 39, and the sum of x+y is from 2 to 78. In preferred embodiments of the invention, the sum of x+y (i.e., the ethylene oxide content of the bisphenol) is from 28 to 34, and most preferably 30, with x and y equal.

The ethoxylated bisphenol, a solid, is melted and then reacted with a member selected from sulfamic acid, sulfuric acid and chlorosulfonic acid. In the reaction, the terminal ethoxylate positions and/or unsubstituted ring positions on the ethoxylated bisphenol are substituted with H⁺SO₃⁻ or NH₄⁺SO₃⁻ groupings depending upon the sulfating agent, which, if desired, can be neutralized to substitute other cationic species for the hydrogen or ammonium ion.

The degree of sulfation attained in the reaction is dependent upon the relative molar ratio between the ethoxylated bisphenol and the sulfating agent, as well as the sulfating agent itself. In the preferred embodiments of the invention, molar ratios between 1:1 and 1:2 are employed, resulting in sulfation at one or each of the terminal ethoxylate positions (—OH terminating) when using sulfamic acid and also generally at one or more ring positions on each aromatic ring using the other sulfating agents.

For the reaction between ethoxylated bisphenol and sulfamic acid (NH₂SO₃H), the reaction generally will be conducted by melting the bisphenol and slowly adding the sulfamic acid thereto. Temperatures generally are maintained at about 70° C. to 80° C. and the reaction typically will be conducted over the course of several hours until all traces of ammonia evolution have ceased.

For the reaction between ethoxylated bisphenol and sulfuric acid, this exothermic reaction is generally conducted with cooling to maintain a reaction temperature of about 15° F. During reaction, free SO₃ combines with the water generated during the (—H+H₂SO₄→H₂O+HSO₃) reaction to form sulfuric acid. When the reaction is complete, the reaction product can be recovered as is or neutralized with, e.g., NaOH or KOH, etc. to substitute for the hydrogen in the HSO₃ group. In the chlorosulfonic acid reaction, the by-product HCl can be removed by washing and the hydrogen in the HSO₃ groups can be substituted for by, e.g., potassium, sodium, lithium, ammonium ion, etc.

The greater the degree of sulfation of the ethoxylated bisphenol, the higher the cloud point for the resultant surfactant in an aqueous electroplating medium. In general, however, increased sulfation may lead to decreased brightness of the deposited metal.

As earlier noted, the surfactant of the present invention is particularly advantageous for use in acid zinc electroplating baths. These aqueous baths operate at a pH of from about 3.0 to about 6.5 and contain a soluble source of zinc ion such as zinc chloride, zinc sulfate, zinc fluoborate, zinc acetate or mixtures thereof. Typically the zinc metal ion will be present in an amount of from about 4 to 100 grams/liter in the bath. The bath also contains a soluble electrolyte, typically an ammonium or alkali metal salt of hydrochloric acid, sulfuric acid, fluoboric acid or mixtures thereof such that the anion electrolyte concentration is from about 15 to about 250 grams/liter.

In these acid zinc baths, a soluble source of an additional metal, such as nickel or copper, also can be present such that the resultant deposit is an alloy of zinc and the additional metal.

The most preferred acid zinc baths, and those in which the advantages of the present invention are most apparent, are those in which the electrolyte is a non-ammoniated electrolyte. In general, these baths can be made completely ammonium-ion free by using an electrolyte composed solely of, e.g., potassium or sodium chloride or can be formulated with low levels of ammonium ion (e.g., less than about 4 grams/liter) in conjunction with the non-ammoniated electrolyte. In either case, it generally will be necessary to further include in the bath boric acid (at least about 1.0 gram/liter) and an organic acid such as benzoic acid, cinnamic acid or the like at a level of about 0.1 to about 15.0 grams/liter. Exemplary formulations of acid zinc plating baths, both ammonium ion-free or ammonium-containing, can be found in U.S. Pat. Nos. 3,729,394, 3,766,024, 3,787,296, 4,070,256 and 4,496,439.

For use as a surfactant in acid zinc baths of this type, as well as in other metal plating baths, the present invention provides a non-ionic compound of the formula:

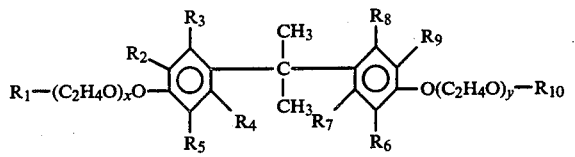

wherein:

x and y are integers from 1 to 39, and the sum of x+y is from 2 to 78;

$R_1$ through $R_{10}$ are H or $SO_3X$, with the proviso that at least one of $R_1$ through $R_{10}$ must be $SO_3X$; and X is any monovalent cation.

The surfactant may be employed as the sole surfactant in the plating bath or in conjunction with other non-ionic surfactants and/or minor amounts of anionic surfactants. Typically, the surfactant of the invention will be present in an amount of from about 2 to 40 grams/liter when used as the sole or predominant surfactant.

The metal electroplating baths in which the surfactant of the present invention is employed preferably will contain a brightener (or grain refining agent as it sometimes is referred to), which may be water-soluble or insoluble or only difficultly soluble, to provide bright deposits over wide-ranging operating conditions. Exemplary brighteners, particularly useful for zinc baths, include ortho-chlorobenzaldehyde, benzylidene acetone, thiophene aldehyde, cinnamic aldehyde, coumarin, as well as other aryl aldehydes, aryl ketones, ring-halogenated derivatives thereof, heterocyclic aldehydes and ketones, and the like. In the preferred embodiment of the invention, the brightener is added to the bath in the form of a microemulsion, as taught in U.S. Pat. No. 4,502,926, incorporated herein by reference.

The surfactant of the invention preferably is admixed with various stabilizers or other functional ingredients used to attain particular effects in the ultimate plating process and in this form then admixed with the other bath components.

In preferred embodiments of the invention, $R_1$ and $R_{10}$ in the surfactant formula are each $SO_3X$ while all other substitution positions $R_2$ through $R_9$ are hydrogen as will be the case with sulfation with sulfamic acid. Also preferred are compounds in which only one of $R_2$, $R_3$, $R_4$ and $R_5$ is $SO_3X$ and only one of $R_6$, $R_7$, $R_8$ and $R_9$ is $SO_3X$. The monovalent cation X may, for example, be hydrogen, ammonium ion, sodium, potassium or lithium.

Further explanation and description of the invention is provided by the following, non-limiting examples.

EXAMPLE 1

An aqueous acid zinc electroplating bath was prepared in accordance with the teachings of U.S. Pat. No. 4,070,256. The bath contained 3.7 oz./gal. zinc chloride, 18 oz./gal. potassium chloride, 3.7 oz./gal. boric acid, and 1% by volume of nonylphenol-ethylene oxide surfactant with benzoic acid added. A brightener consisting of o-chlorobenzaldehyde was added to the bath in the form of a microemulsion so as to attain a level of brightening agent of 75 mg./liter. The microemulsion was prepared in accordance with Example I of U.S. Pat. No. 4,502,926. The pH of the bath was 5.0.

This bath was used to plate zinc on a cathodic workpiece at a bath temperature of 85° F. Excellent plating results were obtained at a brightener consumption rate of 3.7 fluid ounces per 1000 ampere hours of operation.

EXAMPLE 1A

The bath of Example 1 was used to plate zinc on a cathodic workpiece at a bath operating temperature of 110° F. The bath rapidly became cloudy, indicating oiling-out of the non-ionic surfactant component, and the rate of brightener consumption tripled. Operation of the bath was stopped since adequate plating could not be attained at this temperature.

EXAMPLE 2

An aqueous zinc electroplating bath was formulated from zinc chloride (4 oz./gal.), benzoic acid (1.5 g/l), orthochlorobenzaldehyde (0.125 g/l), boric acid (4.0 oz./gal.), potassium chloride (18 oz./gal.) and 5 g/l of a surfactant according to the invention prepared by reacting 2500 grams of ethoxylated bisphenol (30 ethylene oxide units) with 315 grams of sulfamic acid at 72°–78° C. for sixteen hours overnight.

The cloud point of the bath was 160° F.

EXAMPLE 3

An aqueous acid zinc electroplating bath was prepared containing 3.7 oz./gal. zinc chloride, 18.5 oz./gal. potassium chloride, 3.7 oz./gal. boric acid and 0.15% by volume of the ortho-chlorobenzaldehyde of Example 3 of U.S. Pat. No. 4,502,926. To the bath was then added a pre-mixed surfactant component containing 1.68 g/l benzoic acid, 1.68 g/l glycine (to raise the "burn point" of the bath, i.e., the current density at which burning or discoloration of the deposited plate appears), 4.2 g/l of the surfactant prepared as set forth in Example 2, using 1.1 moles sulfamic acid and 1 mole of the ethoxylated bisphenol, 2.1 g/l of the adduct of glycerine and 26 moles ethylene oxide, 0.8 g/l polyethylene oxide (m.w. 1500) and 14.5 g/l xylene sulfonate sodium salt.

The pH of the bath was maintained at 5.2 and the cloud point of the bath was 138° F. The bath was used to plate zinc onto a cathodic workpiece at a bath operating temperature of 95° F. to 100° F. The bath exhibited no foaming and high tolerance to iron contamination. The plated parts exhibited a bright, even deposit with no burning in the high current areas. Chromate adhesion on post-treated parts was excellent, and brightener consumption was at a rate of 1 ml per 2.65 ampere hours.

EXAMPLE 4

In place of the premixed surfactant composition in Example 3, there was prepared for addition to the other bath components a premixed composition of 1.83 g/l benzoic acid, 1.83 g/l glycine, 5.14 g/l of a surfactant prepared according to Example 2, using 1.3 moles sulfamic acid and 1 mole of the ethoxylated bisphenol, 5.1 g/l xylene sulfonate sodium salt, 4.38 g/l of the adduct of glycerine and 26 moles of ethylene oxide, 1.41 g/l of the adduct of thioglycol and 22-23 moles ethylene oxide, and 0.4 g/l of the adduct of beta napthol and 23-26 moles ethylene oxide.

The pH of the bath was maintained at 5.0 and the cloud point of the bath was 160° F. Steel panels were plated with this bath at a bath temperature of 95° F. to 105° F. and panels with a bright, even zinc plate with no burning in the high current density areas were obtained.

EXAMPLE 5

A bath identical in all respects to that of Example 3 was prepared, with the exception that in place of the ortho-chlorobenzaldehyde microemulsion there was used a microemulsion of benzylidene acetone (to provide 125 mg/l of the brightener). The cloud point was 120° F. and excellent plating was obtained at a bath temperature of 110° F.

In the foregoing examples, the grams per liter or ounces per gallon indications for particular components are, of course, with reference to the overall bath composition.

By virtue of the present invention, the cloud point associated with non-ionic surfactants in metal electroplating baths is significantly increased through use of the novel surfactants herein. In this manner, not only may higher temperatures per se be employed to attain advantages associated therewith, but there is also provided great flexibility to the baths which thus keeps the surfactant cloud point from being a limiting factor when formulation or operating changes are proposed to attain particular advantages or effects. Moreover, the surfactants herein confer low foaming properties to metal electroplating baths, confer high tolerance to iron contamination, and also provide improved throwing power at reduced chloride levels.

As noted, the surfactants of the invention have particular suitability with acid zinc plating baths, and especially those formulated to have a low ammonium ion content or to be completely devoid of ammonium ion. Nevertheless, the surfactants herein can be used as all or a portion of the non-ionic surfactant wherever such a component is used in any metal electroplating bath, particularly where a higher operating temperature is desired or where increased flexibility of tolerance to temperature fluctuations is desired. For example, in plating baths where the plating is accompanied by exothermic reactions, the non-ionic surfactants of the present invention will find utility in permitting the elimination or reduction of chillers conventionally employed to keep the bath temperature from exceeding particular operating ranges. In experiments with acid-copper plating baths, cloud points above 130° F. are attained using the surfactants of the invention.

What is claimed is:

1. A compound represented by the formula:

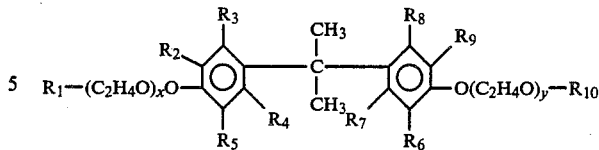

wherein:
 x and y are integers from 1 to 39, and the sum of x+y is from 2 to 78;
 $R_1$ through $R_{10}$ and H or $SO_3X$, with the proviso that at least one of $R_1$ through $R_{10}$ must be $SO_3X$, and X is any monovalent cation.

2. A compound according to claim 1 wherein $R_1$ and $R_{10}$ are $SO_3X$.

3. A compound according to claim 2 wherein each of $R_2$ through $R_9$ is H.

4. A compound according to claim 3 wherein at least one of $R_2$, $R_3$, $R_4$ and $R_5$ is $SO_3X$ and at least one of $R_6$, $R_7$, $R_8$ and $R_9$ is $SO_3X$.

5. A compound according to claim 4 wherein only one of $R_2$, $R_3$, $R_4$ and $R_5$ is $SO_3X$ and only one of $R_6$, $R_7$, $R_8$ and $R_9$ is $SO_3X$.

6. A compound according to claim 1 wherein at least one of $R_2$, $R_3$, $R_4$ and $R_5$ is $SO_3X$ and at least one of $R_6$, $R_7$, $R_8$ and $R_9$ is $SO_3X$.

7. A compound according to any of claims 1 through 6 wherein X is selected from the group consisting of H, $NH_4$, K, Na and Li.

8. A compound according to any of claims 1 through 6 wherein X is $NH_4$.

9. A method for preparing a surfactant useful in electroplating process, comprising contacting under reaction conditions an ethoxylated bisphenol of the formula:

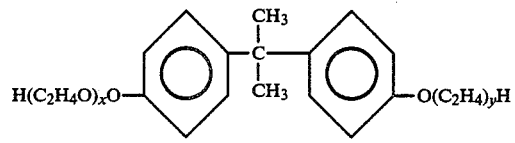

wherein x and y are integers from 1 to 39 and the sum of x+y is from 2 to 78, with a material selected from the group consisting of sulfamic acid, sulfuric acid and chlorosulfonic acid.

10. The method according to claim 9 wherein said material is sulfamic acid.

11. The method according to claim 9 wherein said material is sulfuric acid and wherein the resultant reaction product formed is thereafter neutralized with a hydroxide of a cation selected from the group consisting of $NH_4$, Na, K and Li.

12. The method according to claim 9 wherein said material is chlorosulfonic acid and wherein the resultant reaction product is thereafter freed of associated hydrochloric acid.

13. The reaction products prepared according to the methods of any of claims 9, 10, 11 or 12.

14. A composition for electroplating metal onto a substrate therefor, comprising an aqueous admixture of a soluble source of metal ion; a soluble electrolyte and, as a surfactant, a compound of the formula:

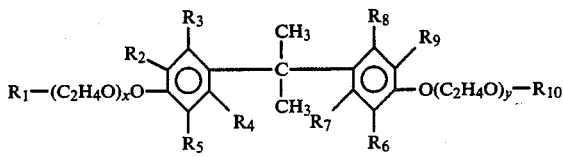

wherein:

x and y are integers from 1 to 39, and the sum of x+y is from 2 to 78;

$R_1$ through $R_{10}$ are H or $SO_3X$, with the proviso that at least one of $R_1$ through $R_{10}$ must be $SO_3X$; and X is any monovalent cation.

15. The electroplating composition according to claim 14 wherein $R_1$ and $R_{10}$ are $SO_3X$.

16. The electroplating composition according to claim 15 wherein each of $R_2$ through $R_9$ is H.

17. The electroplating composition according to claim 15 wherein at least one of $R_2$, $R_3$, $R_4$ and $R_5$ is $SO_3X$ and at least one of $R_6$, $R_7$, $R_8$ and $R_9$ is $SO_3X$.

18. The electroplating composition according to claim 17 wherein only one of $R_2$, $R_3$, $R_4$ and $R_5$ is $SO_3X$ and only one of $R_6$, $R_7$, $R_8$ and $R_9$ is $SO_3X$.

19. The electroplating composition according to claim 14 wherein at least one of $R_2$, $R_3$, $R_4$ and $R_5$ is $SO_3X$ and at least one of $R_6$, $R_7$, $R_8$ and $R_9$ is $SO_3X$.

20. The electroplating composition according to any of claims 14 through 19 wherein X is selected from the group consisting of H, $NH_4$, K, Na and Li.

21. The electroplating composition according to any of claims 14 through 19 further comprising a brightener.

22. The electroplating composition according to any of claims 14 through 19 wherein said soluble electrolyte is a non-ammoniated compound and wherein said metal ion is zinc.

23. A composition for electroplating zinc or an alloy thereof onto a substrate therefor, comprising an aqueous admixture of a soluble source of zinc; a soluble electrolyte; and, as a surfactant, a compound of the formula:

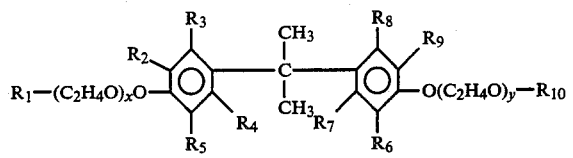

wherein:

x and y are integers from 1 to 39, and the sum of x+y is from 2 to 78;

$R_1$ through $R_{10}$ are H or $SO_3X$, with the proviso that at least one of $R_1$ through $R_{10}$ must be $SO_3X$; and X is any monovalent cation.

24. The electroplating composition according to claim 23 wherein said soluble electrolyte comprises a non-ammoniated compound.

25. The electroplating composition according to claim 23 wherein said composition is completely free of ammonium ion except for ammonium, if any, associated with said surfactant.

26. The electroplating composition according to claims 24 or 25 further comprising boric acid.

27. The electroplating composition according to claims 24 or 25 further comprising an organic acid.

28. The electroplating composition according to claims 23, 24 or 25 further comprising a brightening agent.

29. The electroplating composition according to claims 23, 24 or 25 further comprising a brightening agent added to the composition in the form of a microemulsion.

30. The electroplating composition according to claims 24 or 25 further comprising boric acid, an organic acid and a brightening agent.

31. The electroplating composition according to claims 14 or 23 further comprising xylene sulfonate or salts thereof.

32. A method for electroplating metal onto the surface or surfaces of a substrate, comprising:

(a) preparing an electroplating composition comprising an aqueous solution of a soluble source of metal ion, a soluble electrolyte and, as a surfactant, a compound of the formula:

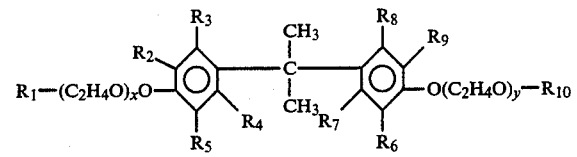

wherein:

x and y are integers from 1 to 39, and the sum of x+y is from 2 to 78;

$R_1$ through $R_{10}$ are H or $SO_3X$ with the proviso that at least one of $R_1$ through $R_{10}$ must be $SO_3X$; and X is any monovalent cation;

(b) maintaining said composition at a temperature suitable for electroplating and below the cloud point of the composition;

(c) immersing into said composition an anode and said substrate; and (d) applying a voltage across the anode and substrate to thereby cause deposition of metal onto the metallic surface or surfaces of said substrate.

33. The method according to claim 32 wherein said metal ion is zinc; said electrolyte is a non-ammoniated electrolyte; and the pH of said composition is from about 3.0 to about 6.5.

34. The method according to claim 32 wherein said composition further comprises boric acid, an organic acid and a brightener.

35. The method according to claim 34 wherein said brightener is present by being added to said composition in the form of a microemulsion.

* * * * *